United States Patent [19]

Suzuki et al.

[11] Patent Number: 5,250,723

[45] Date of Patent: Oct. 5, 1993

[54] HIGH SURFACE HARDNESS TRANSPARENT RESIN AND POLYMERIZABLE MONOMER

[75] Inventors: Toshiyuki Suzuki; Katsuyoshi Sasagawa; Masao Imai; Yoshinobu Kanemura, all of Kanagawa, Japan

[73] Assignee: Mitsui Toatsu Chemicals, Inc., Tokyo, Japan

[21] Appl. No.: 926,300

[22] Filed: Aug. 10, 1992

Related U.S. Application Data

[62] Division of Ser. No. 487,212, Mar. 1, 1990, Pat. No. 5,145,927.

[30] Foreign Application Priority Data

Mar. 1, 1989 [JP] Japan ................... 1-48919
Mar. 20, 1989 [JP] Japan ................... 1-66240
May 26, 1989 [JP] Japan ................... 1-131559

[51] Int. Cl.$^5$ ................ C07C 265/02; C07C 271/00
[52] U.S. Cl. .................... 560/355; 560/33; 560/157; 560/225; 560/357
[58] Field of Search .............. 560/33, 157, 225, 357, 560/355; 526/301, 288

[56] References Cited

U.S. PATENT DOCUMENTS 4,486,582 12/1984 Hefner, Jr. ................ 526/301
4,604,439 8/1986 Colvin et al. ................ 526/301

*Primary Examiner*—Paul R. Michl
*Assistant Examiner*—Tae H. Yoon
*Attorney, Agent, or Firm*—Burns, Doane, Swecker & Mathis

[57] ABSTRACT

A novel polymerizable monomer represented by the formula (I) useful as a raw material for the high surface hardness transparent resin.

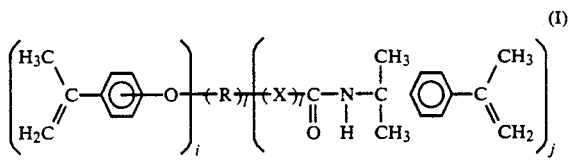

wherein R is an aliphatic residue having or not having an oxygen atom, an alicyclic ring, a heterocyclic ring or an aromatic ring, or an alicyclic residue, l is 0 or 1, each of i and j is an integer of 1 or more, and when l=0, i=j=1, when l=1, (i+j) is 4 or less, when j=1, X is oxygen or sulfur, when j≧2, all X's are oxygen or sulfur, or one X is oxygen and the other X's are sulfur, or one X is sulfur and the other X's are oxygen.

The high surface hardness transparent resin comprises a crosslinked polymer prepared by copolymerizing a monomer (A) represented by the formula (I) as above and a monomer (B) containing one or more functional groups of at least one kind selected from the group consisting of $CH_2=CH-C(O)-O-$, $CH_2=C(CH_3)-C(O)-O-$ and

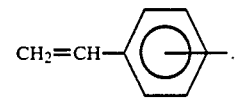

3 Claims, No Drawings

HIGH SURFACE HARDNESS TRANSPARENT RESIN AND POLYMERIZABLE MONOMER

This application is a divisional, of application Ser. No. 07/487,212, filed Mar. 1, 1990 now U.S. Pat. No. 5,145,927.

BACKGROUND OF THE INVENTION (i) Field of the Invention

The present invention relates to a transparent resin which has high surface hardness and exhibits excellent scratch resistance, heat resistance and chemical resistance. The invention also relates to a glazing material, a protective cover for display devices, an optical lens and a hard coat material comprising the resin; and a novel polymerizable monomer useful as a raw material for the high surface hardness transparent resin.

(ii) Description of the Prior Art

Methacrylic resin, polycarbonate resin and polystyrene resin exhibit excellent transparency, impact resistance, workability and mass productivity, and therefore have been used as glazing material such as for windowpanes in vehicles, houses, schools and sports facilities, baseboards of verandas, and balconies, protective covers for display devices such as various dashboards, displays for computers, liquid crystal televisions and front boards of vending machines, optical lenses, illuminator covers, signboards, protective glasses, optical photodisc substrates and the like. Particularly, when the above-mentioned resins are applied as glazing materials, protective covers for display devices and as optical lenses, it is necessary that such resins have high scratch resistance, i.e., high surface hardness, chemical resistance, heat resistance and the like to achieve good visibility and desired appearance, transparency, optical physical properties, mechanical strength, stiffness, and the like.

However, the above-mentioned transparent resins are linear polymers, and therefore do not exhibit the requisite surface hardness, chemical resistance and heat resistance. In addition, even if these resins are coated with a hard coat to improve their surface hardness and chemical resistance, sufficient performance cannot always be obtained.

For the purpose of solving these problems, a transparent resin has been proposed which comprises a polymer having a crosslinking structure such as diethylene glycol diallylcarbonate resin or an urethane polyacrylate (Japanese Patent Laid-open Publication Nos. 3610/1986 and 75022/1988).

However, the proposed resins are prepared by the mutual polymerization of an allyl group, an acrylic group or a methacrylic group, polymerization rates of which are on a similar level, and therefore problems exist such as difficulty in controlling the rate of polymerization, run-away reactions, and a long period of time is required to obtain a polymer having a good surface state and a low polymerization strain.

SUMMARY OF THE INVENTION

The present invention overcomes the problems and disadvantages of the prior art by providing a high surface hardness transparent resin prepared by combining a polymerizable isopropenylphenyl group having a low polymerization rate with another polymerizable group having a high polymerization rate, i.e., by copolymerizing a compound having two or more isopropenylphenyl groups in one molecule thereof and another compound having one or more acryloyl groups, a methacryloyl group and a vinylphenyl group in which the radical polymerizability is higher than in the isopropenylphenyl group. Run-away reaction can be easily controlled at the time of polymerization and the polymerization time can be noticeably reduced.

An object of the present invention is to provide a transparent resin having high surface hardness.

Another object of the present invention is to provide a transparent resin having high surface hardness which can be prepared by an easily controlled polymerization process.

A further object of the present invention is to provide a transparent resin having high surface hardness and excellent chemical resistance.

Still another object of the present invention is to provide a transparent resin having high surface hardness and excellent heat resistance.

An additional object of the present invention is to provide a monomer having a polymerizable group in which the polymerization rate is slower than an acrylic group, a methacrylic group and a vinylphenyl group and which is excellent in copolymerizability with these groups, the aforesaid monomer being also capable of giving a polymer which has high surface hardness and which is excellent in transparency, heat resistance and/or chemical resistance.

Additional objects and advantages of the invention will be set forth in part in the description which follows, and in part will be obvious from the description, or may be learned by practice of the invention. The objects and advantages of the invention will be realized and attained by means of the instrumentalities and combinations, particularly pointed out in the appended claims.

To achieve the objects and in accordance with the purpose of the invention, as embodied and broadly described herein in a first embodiment, the invention provides a high surface hardness transparent resin comprising a crosslinked polymer prepared by copolymerizing a monomer (A) represented by the formula (I)

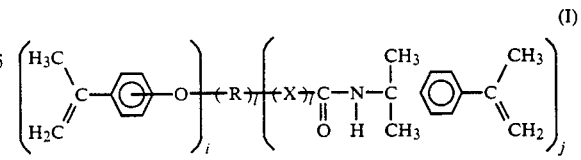

wherein R is an aliphatic residue having or not having an oxygen atom, an alicyclic ring, a heterocyclic ring or an aromatic ring, or an alicyclic residue, l is 0 or 1, each of i and j is an integer of 1 or more, and when l=0, i=j=1, when l=1, (i+j) is 4 or less, when j=1, X is oxygen or sulfur, when j≧2, all X's are oxygen or sulfur or one X is oxygen and the other X or X's are sulfur, or one X is sulfur and the other X or X's are oxygen, and a monomer (B) having one or more functional groups of at least one kind selected from the group consisting of $CH_2=CH-C(O)-O-$, $CH_2=C(CH_3)-C(O)-O-$ and

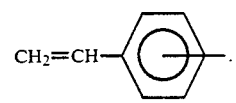

In a second embodiment, the present invention also provides a high surface hardness transparent resin comprising a crosslinked polymer containing a structural unit represented by the following formula (II), (III), (IV) and/or (V) comprising the monomer (A) and the monomer (B) set forth above.

lic ring, a heterocyclic ring or an aromatic ring, or an alicyclic residue, l is 0 or 1, each of i and j is an integer of 1 or more, and when l=0, i=j=1, when l=1, (i+j) is 4 or less, when j=1, X is oxygen or sulfur, when j≧2, all X's are oxygen or sulfur, or one X is oxygen and the other X or X's are sulfur, or one X is sulfur and the other X or X's are oxygen.

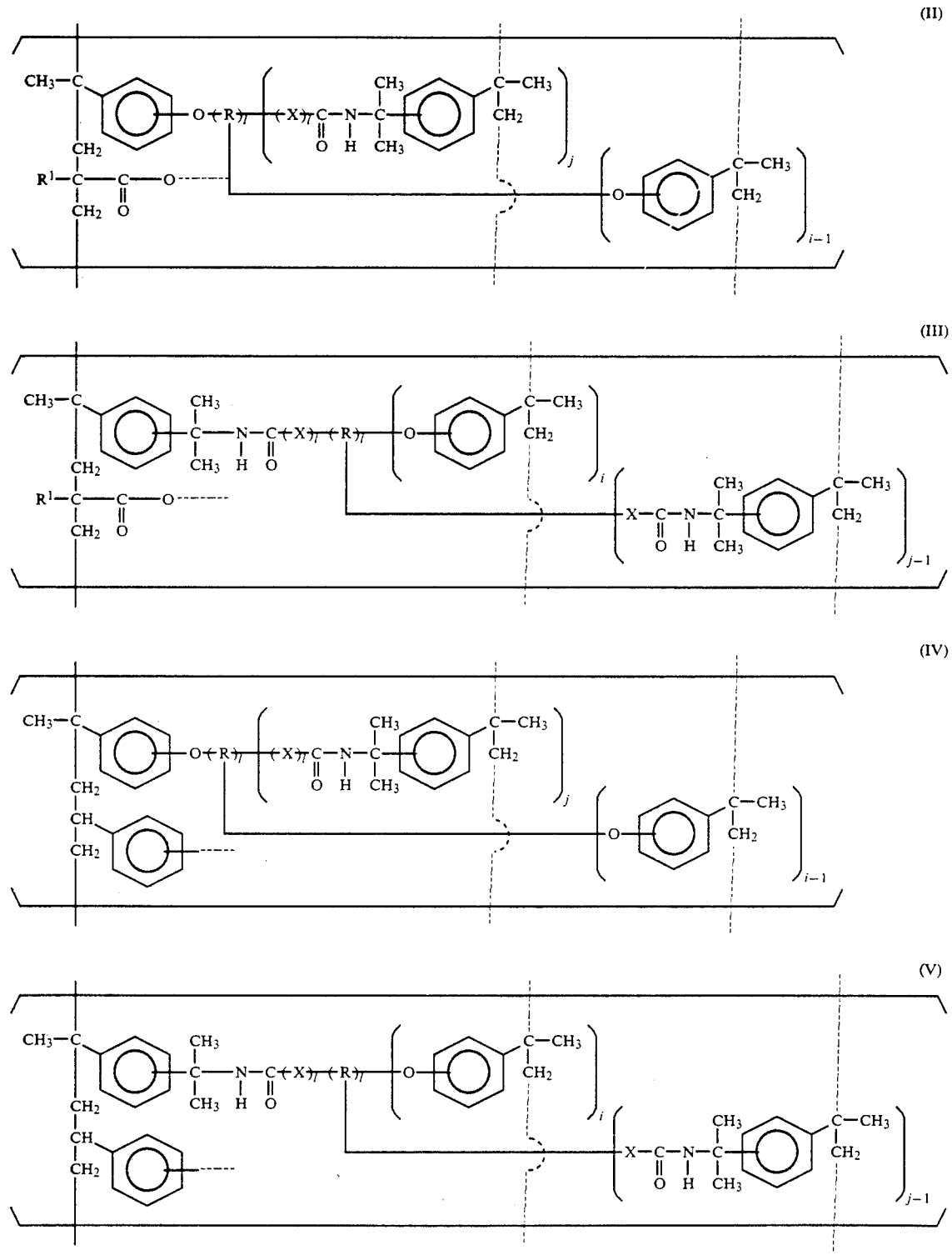

wherein R¹ is hydrogen or methyl, R is an aliphatic residue having or not having an oxygen atom, an alicyc- In another embodiment, the present invention provides a glazing material comprising a high-hardness transparent resin described in the first embodiment of the invention.

In a fourth embodiment, the present invention also provides a protective cover for display devices comprising the high-hardness transparent resin described in the first embodiment of the present invention.

In a fifth embodiment the present invention provides an optical lens comprising the high-hardness transparent resin described in the first embodiment of the present invention.

In a sixth embodiment the present invention provides a hard coat material comprising the high-hardness transparent resin described in the first embodiment of the present invention.

In a seventh embodiment, the present invention provides a high-hardness transparent resin comprising a crosslinked polymer prepared by copolymerizing a monomer (A) selected from the group consisting of monomers represented by the formulae (VI) and (VII), and a monomer (B) having, in one molecule, one or more functional groups selected from the group consisting of $CH_2=CH-C(O)-O-$, $CH_2=C(CH_3)-C(O)-O-$ and

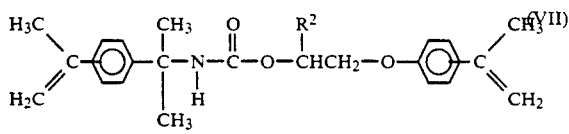

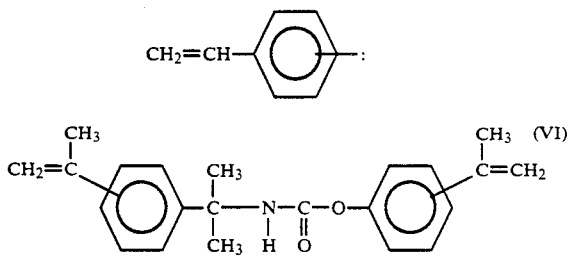

(VI)

wherein the substituents on the aromatic ring of the isopropenyl-α, α-dimethylbenzyl group are present at the m-position or p-position thereof, and the substituents on the aromatic ring of the isopropenylphenoxy group are present at the o-position, m-position or p-position thereof,

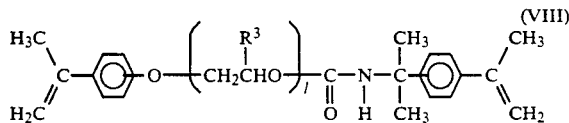

(VII)

wherein $R^2$ represents —H or —CH$_3$, the substituents on the aromatic ring of isopropenyl-α, α-dimethylbenzyl group are present at the m-position or p-position thereof, and the substituents on the aromatic ring of the isopropenylphenoxy group are present at the o-position m-position or p-position thereof.

In an eight embodiment, the present invention is directed to a polymerizable monomer represented by the formula (I), especially the formula (VIII) below:

(VIII)

$$H_3C\diagdown_{C}-\bigcirc-O-\left(CH_2CHO\right)_l-C-N-C-\bigcirc-C\diagup^{CH_3}_{CH_2}$$
$$H_2C\diagup \quad R^3 \quad \quad O \ H \ CH_3$$

wherein l is 0 or 1, $R^3$ represents —H or —CH$_3$, and the substituents on the aromatic ring of the isopropenyl-α, α-dimethylbenzyl group are present at the m-position or p-position thereof, and the substituents on the aromatic ring of the isopropenylphenoxy group are present at the o-position, m-position or p-position thereof.

In addition, it has also been found that the resin of the present invention has a high surface hardness, i.e., scratch resistance, heat resistance, and chemical resistance, and therefore plate materials comprising this resin are useful as glazing materials such as windowpanes of vehicles, houses, schools and sports facilities, baseboards of verandas, and balconies, protective covers for display devices such as various dashboards, displays for computers, liquid crystal televisions and front boards of vending machines, and in the case of a lens-like shaped polymer, optical lenses. Furthermore, it has been found that the resin of the present invention is also useful as a coating film, i.e., hard coat material, because when the resin is applied onto a resin, a metal or a lumber material and then polymerized, the obtained hard coat has excellent scratch resistance and chemical resistance.

DESCRIPTION OF THE PREFERRED EMBODIMENTS

Reference will now be made in detail to the present preferred embodiments of the invention.

Exemplary suitable monomer (A) represented by the formula (I) for use in the present invention.

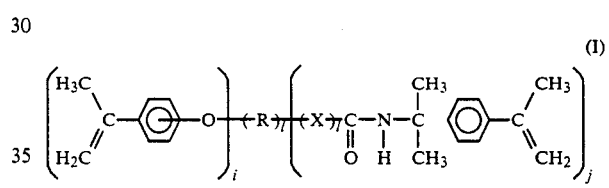

(I)

wherein R is an aliphatic residue having or not having an oxygen atom, an alicyclic ring, a heterocyclic ring or an aromatic ring, or an alicyclic residue, l is 0 or 1, each of i and j is an integer of 1 or more, and when l=0, i=j=1, when l=1, (i+j) is 4 or less, when j=1, X is oxygen or sulfur, when j≧2, all X's are oxygen or sulfur, or one X is oxygen and the other X or X's are sulfur, or one X is sulfur and the other X or X's are oxygen, include (1) a compound obtained by reacting isopropenyl phenol with isopropenyl-α, α-dimethylbenzyl isocyanate, i.e., a carbamic acid esterification reaction between the phenolic hydroxyl group in isopropenylphenol and the isocyanate group in isopropenyl-α, α-dimethylbenzyl isocyanate, (2) a compound obtained by opening the ring of a compound having an aliphatic residue having or not having an oxygen atom, an alicyclic ring, a heterocyclic ring or an aromatic ring or an alicyclic residue and having one or two of an epoxy group and a thiirane group by the use of isopropenylphenol, and then performing a carbamic acid esterification reaction or a thiocarbamic acid esterification reaction between the resulting OH group or SH group and the isocyanate group in isopropenyl-α, α-dimethylbenzyl isocyanate, and (3) a compound obtained by carrying out an etherification reaction between isopropenylphenol and a compound having an aliphatic residue having or not having an oxygen atom, an alicyclic ring, a heterocyclic ring or an aromatic ring, or an alicyclic residue and having one or more alkyl halide groups, reactive with the phenolic hydroxyl group in isopropenylphenol and one or more OH groups and/or SH groups i.e., between the alkyl halide group and the phenolic hydroxide group in isopropenylphenol, and then performing a carbamic acid esterification reaction and/or a thiocarbamic acid esterification reaction of the OH group and/or the SH group with the isocyanate group in isopropenyl-α, α-dimethylbenzyl isocyanate. Here, there are included the compounds of the formula (I) in which when i=1, j=2 or 3, all X's are oxygen or sulfur, or one X is oxygen or sulfur and the remaining X or X's are sulfur or oxygen.

Usually, the lower the molecular weight of the residue R in the formula (I), the better, depending upon the steric firmness of its structure, Preferably, the molecular weight of the residue R is from 25 to 500.

Exemplary suitable compounds having an aliphatic residue having or not having an oxygen atom, an alicyclic ring, a heterocyclic ring or an aromatic ring, or an alicyclic residue and having one or two of an epoxy group and a thiirane group for use in the invention include ethylene oxide, propylene oxide, 2,3-epoxybutane, 3,4-epoxybutane, 2,3-epoxypentane, 1,2-epoxyhexane, epoxycyclohexane, epoxycycloheptane, epoxycyclooctane, styrene oxide, 2-phenyl-1, 2-epoxypropane, tetramethylethylene oxide, epichlorohydrin, epibromohydrin, glycidol, 1,2-epoxy-3-phenoxypropane, glycidyl isopropyl ether, ethylene sulfide, propylene sulfide, isobutene sulfide, 2,3-butylene sulfide, styrene sulfide, ethylene glycol diglycidyl ether, butanediol diglycidyl ether, neopentyl glycol diglycidyl ether, spiroglycol diglycidyl ether, bisphenol A epoxy resin, tetrabromobisphenol A epoxy resin, bisphenol F epoxy resin, bisphenol S epoxy resin, alicyclic diepoxyacetal, alicyclic diepoxy adipate, alicyclic diepoxy carboxylate, vinylcyclohexene dioxide, diglycidyl phthalate, diglycidyl tetrahydrophthalate, diglycidyl hexahydrophthalate, glycidyl p-glycidyloxybenzoate, diglycidyl malonate, diglycidyl succinate, diglycidyl glutarate, diglycidyl adipate, N,N-diglycidylaniline and diglycidyl hydantoin.

Examples of the compound having an aliphatic residue or an alicyclic residue having one or more of an alkyl halide group reactive with the phenolic hydroxyl group in isopropenylphenol and one or more of an OH group and/or SH group and having or not having an oxygen atom, an aliphatic ring, a heterocyclic ring or an aromatic ring include iodoethanol, bromoethanol, bromopropanol, 3-bromo-1,2-propandiol, bromohexanol, chloroethanol, chloropropanol, 3-chloro-1, 2-propandiol, chlorobutanol, chlorohexanol, 1,4-dibromo-2,3-butanediol, 2,3-dibromo-1,4-butanediol, 1,4-dibromo-2-butanol, 1,3-dibromo-2-propanol, 2,3-dibromopropanol, 1,3-dichloro-2-propanol, dibromoneopentyl glycol and chloropropanethiol, 3-chloro-2-hydroxypropanethiol and 3-bromo-2-hydroxypropanethiol.

The monomer (A) can be obtained by the use of the above-mentioned compounds (1), (2) and (3) in accordance with a known carbamic acid esterification, thiocarbamic acid esterification, etherification and ring-opening reaction of the epoxy group or thiirane group. When a solvent is used, the solvent should be distilled off after the synthetic reactions. If necessary, purification is additionally carried out. The thus obtained monomer (A) is ready for the subsequent radical polymerization.

Other examples of the monomer (A) include compounds represented by the following formula in addition to the above-mentioned compounds represented by formulas (VI) and (VII):

Further examples of the monomer (A) are as shown below.

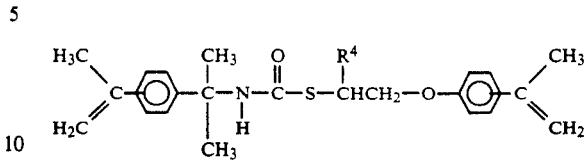

(wherein R⁴ is —H or —CH₃, the substituents on the aromatic ring of the isopropenyl-α, α-dimethylbenzyl group are at the m-position or p-position thereof, and those of the isopropenylphenoxy group are p-, m-, or o-position thereof),

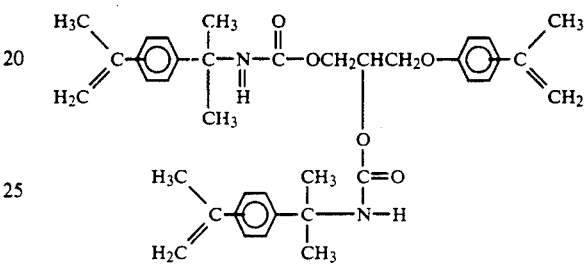

(wherein the substituents on the aromatic ring of the isopropenyl-α, α-dimethylbenzyl are at the m- or p-position, and those of the isopropenylphenoxy group are at the p-, m-, o-position),

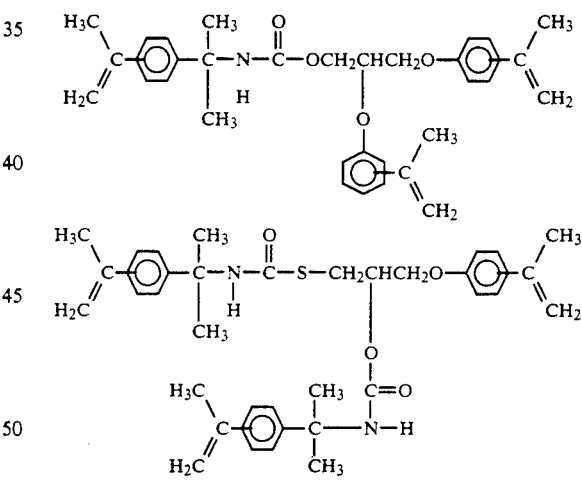

The positions of the substituents on the aromatic rings in the above two formulas are as defined above.

The monomer B having one or more functional groups of at least one kind selected from the group consisting of CH₂=CH—C(O)—O—, CH₂=C(CH₃)—C(O)—O— and

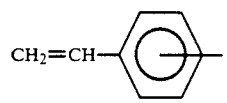

in one molecule in the present invention is an ester of acrylic acid or methacrylic acid or a derivative of styrene. Exemplary suitable monomer (B) include methyl acrylate, methyl methacrylate, ethyl acrylate, ethyl methacrylate, propyl acrylate, propyl methacrylate, isopropyl acrylate, isopropyl methacrylate, cyclohexyl acrylate, cyclohexyl methacrylate, benzyl acrylate, benzyl methacrylate, methoxyethyl acrylate, methoxyethyl methacrylate, ethoxyethyl acrylate, ethoxyethyl methacrylate, 2-hydroxyethyl acrylate, 2-hydroxyethyl methacrylate, 2-hydroxypropyl acrylate, 2-hydroxypropyl methacrylate, 1,4-butylene glycol monoacrylate, 1,4-butylene glycol monomethacrylate, glycidyl acrylate, glycidyl methacrylate, styrene, methylstyrene, chlorostyrene, bromostyrene, chloromethylstyrene, methoxystyrene, ethylene glycol diacrylate, ethylene glycol dimethacrylate, diethylene glycol diacrylate, diethylene glycol dimethacrylate, propylene glycol diacrylate, propylene glycol dimethacrylate, dipropylene glycol diacrylate, dipropylene glycol dimethacrylate, 2, 2-bis(4-acryloxyethoxyphenyl)propane, 2,2-bis(4-methacryloxy-ethoxyphenyl)propane, 2,2-bis(4-acryloxydiethoxyphenyl)propane, 2,2-bis(4-methacryloxydiethoxy-phenyl)propane, 2,2-bis(4-acryloxypropyloxyphenyl)propane, 2,2-bis (4-methacryloxypropyloxyphenyl)propane, 1,3-butane-diol diacrylate, 1,3-butanediol dimethacrylate, 1,4-butanediol diacrylate, 1,4-butanediol dimethacrylate, 1,6-hexanediol diacrylate, 1,6-hexanediol dimethacrylate, neopentyl glycol diacrylate neopentyl glycol dimethacrylate, neopentylglycol hydroxypivalate diacrylate, spiroglycol diacrylate, spiroglycol dimethacrylate, epoxy acrylate epoxy methacrylate, 2-propenoic acid [2-[1,1-dimethyl-2-[(1-oxo-2-propenyl)oxy)ethyl]-5-ethyl-1,3-dioxane-5-yl]methyl ester, trimethylolpropane triacrylate, trimethylolpropane trimethacrylate, pentaerythritol triacrylate, pentaerythritol trimethacrylate, bis(acryloyloxyethyl)hydroxyethyl isocyanurate, bis (methacryloyloxyethyl)hydroxyethyl isocyanurate, tris(acryloyloxy -ethyl)isocyanurate, tris(methacryloyloxyethyl) isocyanurate, pentaerythritol tetraacrylate, pentaerythritol tetramethacrylate, dipentaerythritol hexaacrylate, dipentaerythritol hexamethacrylate, methyltri(acryloyloxyethoxy)silane, glycerol diacrylate, glycerol dimethacrylate, glycerol methacrylate acrylate, dibromoneopentyl glycol diacrylate, dibromoneopentyl glycol dimethacrylate, divinylbenzene, urethane acrylates, urethane methacrylates, 1,1,3,3,5,5-hexa(acryloyloxy)cyclotriphosphazene, 1,1,3,3,5,5-hexa(methacryloyloxy)cyclotriphosphazene, 1,1,3,3,5,5-hexa(acryloylethylenedioxy) cyclotriphosphazene and 1,1,3,3,5,5-hexa(methacryloylethylenedioxy) cyclotriphosphazene.

In the present invention, a transparent resin having a high surface hardness can be prepared by copolymerizing a monomer (A) represented by the formula (I)

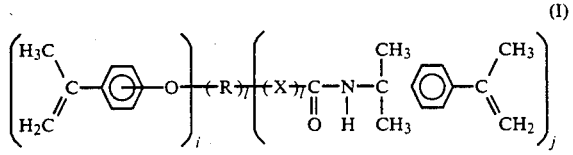

(I)

where R, X, i, l and j are as defined above for the formula (I) and a monomer B having one or more functional groups selected from the group consisting of $CH_2=CH-C(O)-O-$, $CH_2=C(CH_3)-C(O)-O-$ and

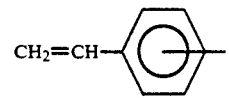

For the purpose of adjusting viscosity and the like, monomer having an isopropenylphenyl group other than the above-mentioned monomer (A) may be additionally used. Exemplary suitable additional monomers include diisopropenylbenzene, N-(3-isopropenyl-α, α-dimethylbenzyl)-2-acryloyloxy carbamate and N-(3-isopropenyl-α, α-dimethylbenzyl)-2-methacryloyloxy carbamate.

In this copolymerization, the ratio of the isopropenyl group to $CH_2=CH-C(O)-O-$, $CH_2=C(CH_3)-C(O)-O-$ and

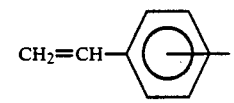

in a mixture of the above-mentioned monomers depends on the types of functional groups in the monomers and the structures of the monomers. Preferably, the copolymerization is carried out in a ratio of the isopropenylphenyl group: the total of $CH_2=CH-C(O)-O-$, $CH_2=C(CH_3)-C(O)-O-$ and

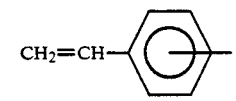

of 1 equivalent: 0.5–10 equivalents.

The copolymerization in the present invention is a radical copolymerization and can be accomplished by heat polymerization or by a means using ultraviolet rays or γ rays, or a combination thereof.

When the heat polymerization is carried out, a known radical polymerization initiator can optionally be used. Exemplary suitable initiators include peroxides such as benzoyl peroxide, p-chlorobenzoyl peroxide, diisopropyl peroxy carbonate, di-2-ethylhexyl peroxy carbonate and t-butylperoxy pivalate as well as azo compounds such as azobisisobutyronitrile. This initiator is preferably used in an amount of from 0.01 to 5% weight.

When the ultraviolet rays are utilized, a known optical sensitizer can optionally be used. Exemplary suitable sensitizers include benzoyl compounds, benzoin methyl ether, benzoin ethyl ether, benzoin propyl ether, benzoin isobutyl ether, 2-hydroxy-2-benzoylpropane, azobisisobutyronitrile, benzil, thioxanthone and diphenyl disulfide. This sensitizer is used in an amount of from 0.01 to 5% by weight.

When γ rays are utilized, the polymerization initiator and the like are not always necessary.

In the present invention, plates or lenses containing the high surface hardness transparent resin of the invention can be prepared by known optional processes. A typical process is a casting polymerization process. For example, a mixture of the above-mentioned monomers is mixed with a radical polymerization initiator or an optical sensitizer sufficiently, followed by defoaming. Afterward, the mixture is poured into a glass or metallic mold with which a gasket or a spacer is combined, and is then cured by heating or irradiation of ultraviolet rays or radiation. Additives may be added to the mixture prior to polymerization. Exemplary suitable additives include ultra-violet absorbents, a oxidation inhibitors, dyes, near infrared absorbents, release agents and antistatic agents. These additives should be used in amounts such that they do not prevent the polymerization and curing.

When the high surface hardness transparent resin of the invention is used for the preparation of coating films, a known coating film manufacturing process may be employed. For example, a radical polymerization initiator or an optical sensitizer is added to a mixture of the above-mentioned monomers, and if necessary, the mixture is diluted with a solvent. Afterward, a substrate made of a resin, a metal, a lumber material or the like is coated with the mixture by roll coating, spray coating, flow coating, dipping or the like. When the solvent is used, it is volatilized, and curing is then carried out by heating or by the irradiation of ultraviolet rays or radiation. In this case, additives, a filler and the like can be added to the mixture prior to the polymerization. Exemplary suitable additives include ultraviolet absorbents, oxidation inhibitors, dyes, pigments, near infrared absorbents, antistatic agents and fine inorganic compound grains. These additives should be used in amount such that they do not prevent polymerization and curing.

The thus obtained high surface hardness transparent resin plate can be used as a glazing material a protective cover for display devices and the like and has high scratch resistance, chemical resistance, heat resistance and excellent workability. In addition, when polymerization is carried out in a mold for lenses, or when the resin is processed by cutting and polishing optical lenses having the same characteristics as in the above case can be obtained.

Moreover, the high-hardness transparent resin can be used as a coating material, i.e., a hard coat material that exhibits excellent scratch resistance, chemical resistance and the like on another resin, a metal, a lumber material or the like.

The novel polymerizable monomer of the present invention is the above mentioned monomer (A). Exemplary suitable monomer include [N-(3-isopropenyl-α, α-dimethylbenzyl)](4-isopropenylphenyl) carbamate, [N-(3-isopropenyl-α, α-dimethylbenzyl)](3-isopropenylphenyl) carbamate, [N-(3-isopropenyl-α, α-dimethylbenzyl)](2-isopropenyl) carbamate, [N-(4-isopropenyl-α, α-dimethylbenzyl)](4-isopropenylphenyl) carbamate, [N-(4-isopropenyl-α, α-dimethylbenzyl)](3-isopropenylphenyl) carbamate, [N-(4-isopropenyl-α, α-dimethylbenzyl)](2-isopropenylphenyl) carbamate, N-(3-isopropenyl-α, α-dimethylbenzyl) [2-(4-isopropenylphenoxy) ethyl] carbamate, N-(3-isopropenyl-α, α-dimethylbenzyl)[2-(3-isopropenylphenoxy)ethyl] carbamate, N-(3-isopropenyl-α, α-dimethylbenzyl)[2-(2-isopropenylphenoxy)ethyl] carbamate, N-(4-isopropenyl-α, α-dimethylbenzyl) [2-(4-isopropenylphenoxy)ethyl] carbamate, N-(4-isopropenyl-α, α-dimethylbenzyl)[2-(3-isopropenylphenoxy)ethyl] carbamate, N-(4-isopropenyl-α, α-dimethylbenzyl) [2-(2-isopropenylphenoxy)ethyl] carbamate, N-(3-isopropenyl-α, α-dimethylbenzyl)[1-(4-isopropenylphenoxy)-1-methylthyl] carbamate, N-(3-isopropenyl-α, α-dimetylbenzyl)-[1-(3-isopropenylphenoxy)-2-methylethyl] carbamate, N-(3-isopropenyl-α, α-dimethylbenzyl)[2-(2-isopropenyl-phenoxy)-1-methylethyl] carbamate, N-(4-isopropenyl-α, α-dimethylbenzyl)[1-(4-isopropenyl-phenoxy)-1-methylethyl] carbamate, N-(4-isopropenyl-α, α-dimethylbenzyl)[2-((3-isopropenylphenoxy)-1-methylethyl] carbamate and N-(4-isopropenyl-α, α-dimethylbenzyl)[1-(2-isopropenylphenoxy)-1-methylethyl] carbamate and the like.

The above-mentioned polymerizable monomer of the present invention can be prepared by reacting 3-isopropenyl-α, α-dimethylbenzyl isocyanate or 4-isopropenyl-α, α-dimethylbenzyl isocyanate with 4-isopropenylphenol, 3-isopropenylphenol or 2-isopropenylphenol or 2-(4-isopropenylphenoxy) ethanol, 2-(3-isopropenylphenoxy) ethanol, 2-(2-isopropenylphenoxy) ethanol, 2-(4-isopropenylphenoxy)-1-methyl ethanol, 2-(3-isopropenylphenoxy)-1-methyl ethanol or 2-(2-isopropenylphenoxy)-1-methyl ethanol obtained by the reaction of 4-isopropenylphenol, 3-isopropenylphenol, 2-isopropenylphenol, with ethylene oxide, ethylene bromohydri or propylene oxide, in the absence of any solvent or in the presence of a solvent such as hexane, chloroform, benzene or toluene unreactive with the raw materials in a ratio of 0.8 to 1.0 equivalent, preferably 0.95–1.0 equivalent to one equivalent of 4-isopropenylphenol, 3-isopropenylphenol, 2-isopropenylphenol or the above-mentioned hydroxy ether to 0.8 to 1.0 equivalent, preferably from 0.95 to 1.0 equivalent of the above-mentioned isocyanate, at a reaction solution temperature of from 30° to 150° C., preferably from 50° to 100° C. in the absence of any catalyst or in the presence of a catalyst to accelerate urethane formation such as dibutyltin dilaurate in an amount of 0.01 to 5% by weight, preferably from 0.1 to 3% by weight based on the weight of the isocyanate. After completion of the reaction, the resulting reaction solution is purified by column chromatography, whereby the desired polymerizable monomer of the present invention can be obtained.

The resin of the present invention has a high surface hardness and is excellent in transparency, chemical resistance and heat resistance. In addition, it is also excellent in workability such as cutting owing to the high surface hardness.

Moreover, in the preparation of the resin of the present invention, polymerization control in the polymerization step is very easy, and therefore peeling, whiting and cracking do not occur in the molding polymerization.

The resin of the present invention exhibits very good moldability and therefore highly accurate molding is possible.

Thus, the resin of the present invention can be suitably used as a glazing material, a protective cover for display devices, an optical lens and a hard coat material.

Furthermore, when the novel polymerizable monomer of the present invention is copolymerized with a monomer having a polymerizable group in which the polymerization rate is high, for example, an acrylic group, a methacrylic group or a vinylphenyl group a transparent resin can be obtained which has a high surface hardness and which is excellent in heat resistance and workability such as cutting. Additionally the polymerization control is very easy. Therefore, the monomer of the present invention is useful as the raw material of the above-mentioned high-hardness transparent resin.

The invention will be further clarified by the following examples, which are intended to be purely examplary of the invention.

EXAMPLES

Reference will be first to each novel polymerizable monomer (Δ) of the present invention. In the examples, part and parts are by weight unless otherwise specified.

Example 1

13.4 parts of 4-isopropenylphenol, 50 parts of toluene, 20.1 parts of 3-isopropenyl-α, α-demethylbenzyl isocyanate and 0.3 part of dibutyltin dilaurate were mixed. The mixture was then stirred for 3 hours, while a reaction solution temperature was maintained at 100° C., to carry out the reaction. After completion of the reaction, the reaction solution was concentrated. The resulting concentrate of then purified by chromatography, thereby obtaining 20.9 parts of [N-(3-isopropenyl-α, α-dimethylbenzyl] (4-isopropenylphenyl) carbamate in the state of a white solid.

| Values of elemental analysis (as $C_{22}H_{25}NO_2$) | | | |
|---|---|---|---|
| | C | H | N |
| Found (%) | 78.59 | 7.55 | 4.09 |
| Calcd. (%) | 78.77 | 7.51 | 4.18 |

NMR (δ/CDCl₃)

$\delta = 1.75$ (s, 6H, C$\underline{H}_3$—C—CH$_3$).

2. 10 (s, 3H, 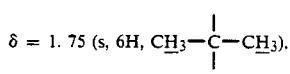 ), 2. 16 (s, 3H, 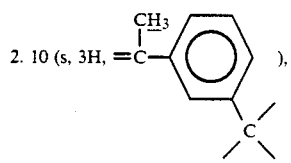 ), 5. 03 (s, 1H, 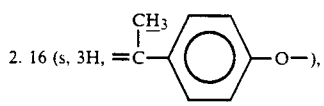 ), 5. 09 (s, 1H, 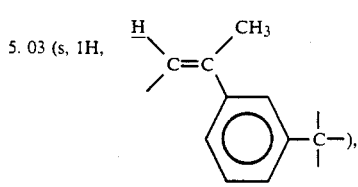 ), 5. 28 (s, 1H, 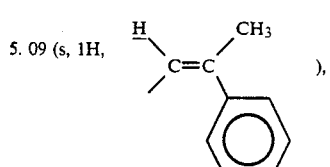 ), 5. 36 (s, 1H, 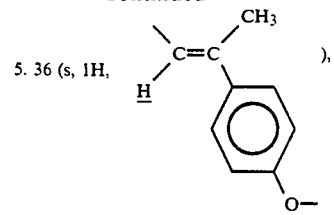 ), 5. 44 (s, 1H, —N—), 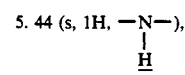

6. 90 ~ 7. 60

(m, 8H, 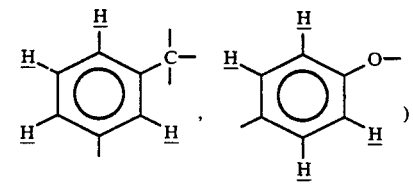 )

Example 2

The same procedure as in Example 1 was repeated except that 13.4 parts of 4-isopropenylphenol in Example 1 was replaced with 13.4 parts of 3-isopropenylphenol, thereby obtaining 24.1 parts of [N-(3-isopropenyl-α,α-dimethylbenzyl)](3-isopropenylphenyl) carbamate in the form of a colorless liquid.

| Values of elemental analysis (as $C_{22}H_{25}NO_2$) | | | |
|---|---|---|---|
| | C | H | N |
| Found (%) | 78.68 | 7.57 | 4.21 |
| Calcd. (%) | 78.77 | 7.51 | 4.18 |

NMR (δ/CDCl₃)

$\delta = 1.74$ (s, 6H, C$\underline{H}_3$—C—CH$_3$).

2. 11 (s, 3H, 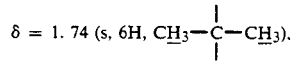 ), 2. 16 (s, 3H, 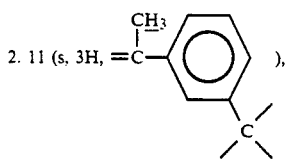 ), 5. 06 (s, 2H, 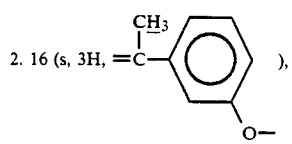 ,

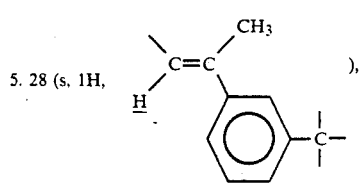

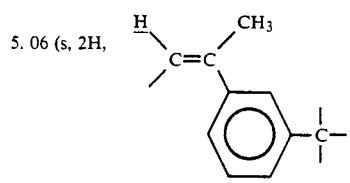

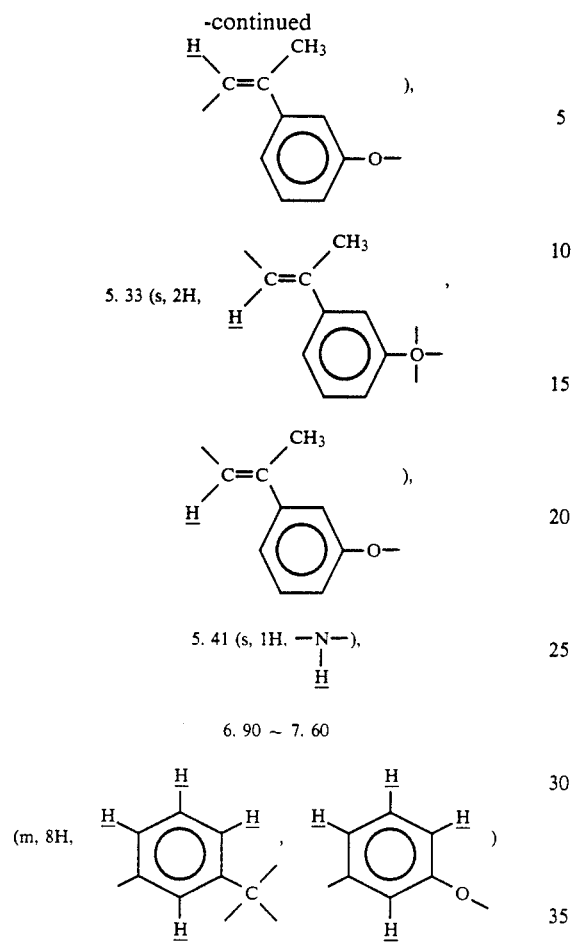

6.90 ~ 7.60

Example 3

The same procedure as in Example 1 was repeated that 13.4 parts of 4-isopropenylphenol in Example replaced with 13.4 parts of 2-isopropenylphenol, obtaining 22.7 parts of [N-(3-isopropenyl-α-dimethylbenzyl)](2-isopropenylphenyl) carbamate in the form of a colorless liquid.

| Values of elemental analysis (as C$_{22}$H$_{25}$NO$_2$) | | | |
|---|---|---|---|
| | C | H | N |
| Found (%) | 78.74 | 7.45 | 4.15 |
| Calcd. (%) | 78.77 | 7.51 | 4.18 |

NMR (δ/CDCl$_3$)

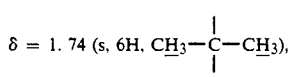

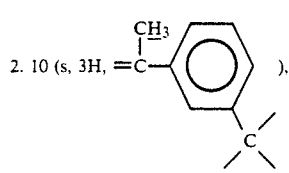

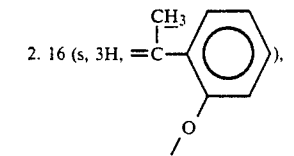

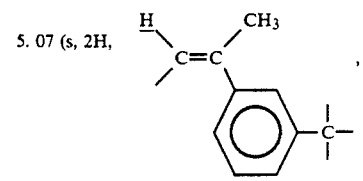

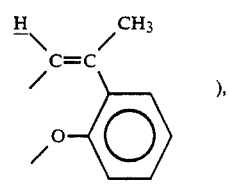

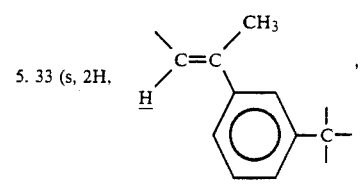

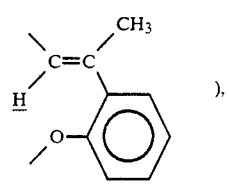

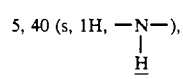

7,00 ~ 7,60

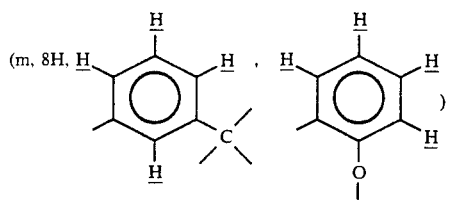

Example 4

13.4 parts of 4-isopropenylphenol, 50 parts of toluene, 20.1 parts of 4-isopropenyl-α,α-dimethylbenzyl part of dibutyltin dilaurate were mixed.

The mixture was then stirred for 3 hours, while a solution temperature was maintained at 100° C., to reaction. After completion of the reaction, the reaction was concentrated. The resulting concentrate was then purified chromatography, thereby obtaining 23.4 parts of [N-(4-isopropenyl-α,α-dimethylbenzl)](4carbamate in the form of a white solid.

| Values of elemental analysis (as $C_{22}H_{25}NO_2$) | | | |
|---|---|---|---|
| | C | H | N |
| Found (%) | 78.62 | 7.57 | 4.23 |
| Calcd. (%) | 78.77 | 7.51 | 4.18 |

NMR (δ/CDCl₃)

δ = 1.74 (s, 6H, 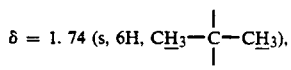), 2.09 (s, 3H, 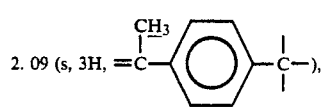), 2.15 (s, 3H, 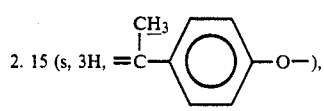), 5.04 (s, 1H, 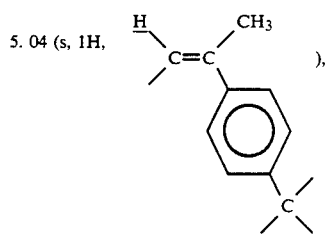), 5.10 (s, 1H, 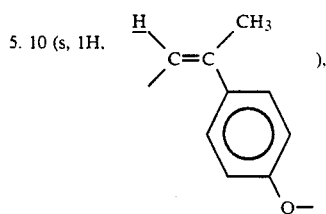), 5.30 (s, 1H, 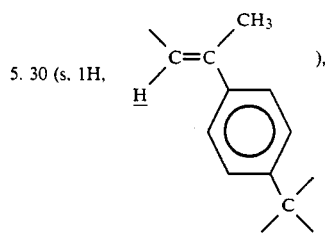), 5.37 (s, 1H, 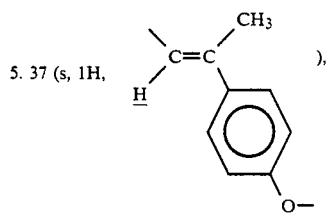), 5.44 (s, 1H, 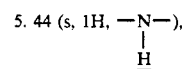), 6.85 ~ 7.50

(m, 8H, 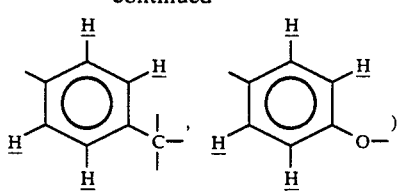)

Example 5

The same procedure as in Example 4 was repeated that 13.4 parts of 4-isopropenylphenol in Example replaced with 13.4 parts of 3-isopropenylphenol, obtaining 25.2 parts of [N-(4-isopropenyl-α-dimethylbenzyl)](3-isopropenylphenyl) carbamate in the form of a colorless liquid.

| Values of elemental analysis (as $C_{22}H_{25}NO_2$) | | | |
|---|---|---|---|
| | C | H | N |
| Found (%) | 78.52 | 7.70 | 4.31 |
| Calcd. (%) | 78.77 | 7.51 | 4.18 |

NMR (δ/CDCl₃)

δ = 1.75 (s, 6H, 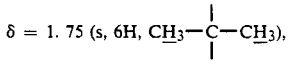), 2.10 (s, 3H, 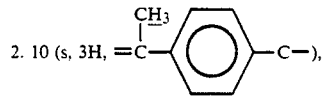), 2.15 (s, 3H, 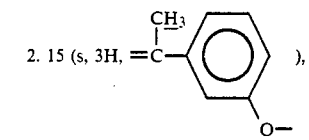), 5.08 (s, 2H, 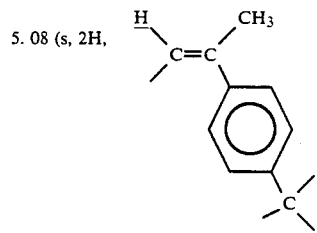),

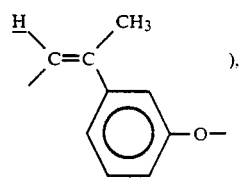),

-continued

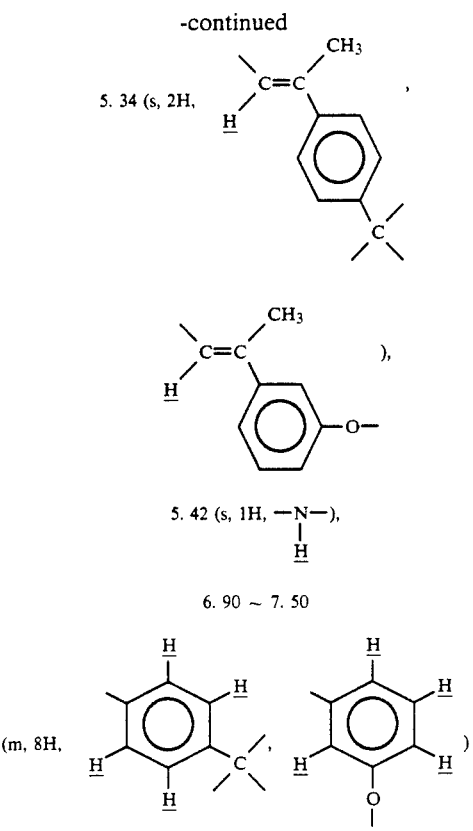

5.34 (s, 2H, ...),

), 5.42 (s, 1H, —N—H), 6.90 ~ 7.50

(m, 8H, ...)

Example 6

The same procedure as in Example 4 was repeated that 13.4 parts of 4-isopropenylphenol in Example replaced with 13.4 parts of 2-isopropenylphenol, obtaining 24.9 parts of [N-(4-isopropenyl-α-dimethylbenzyl)](2-isopropenylphenyl) carbamate in the form of a colorless liquid.

| Values of elemental analysis (as $C_{22}H_{25}NO_2$) | | | |
|---|---|---|---|
| | C | H | N |
| Found (%) | 78.67 | 7.33 | 4.24 |
| Calcd. (%) | 78.77 | 7.51 | 4.18 |

NMR(δ/CDCl₃)

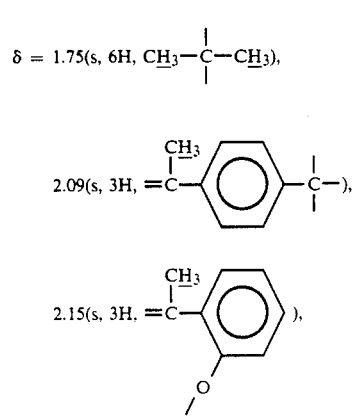

$\delta$ = 1.75(s, 6H, $C\underline{H}_3$—C—$C\underline{H}_3$), 2.09(s, 3H, ...), 2.15(s, 3H, ...), -continued

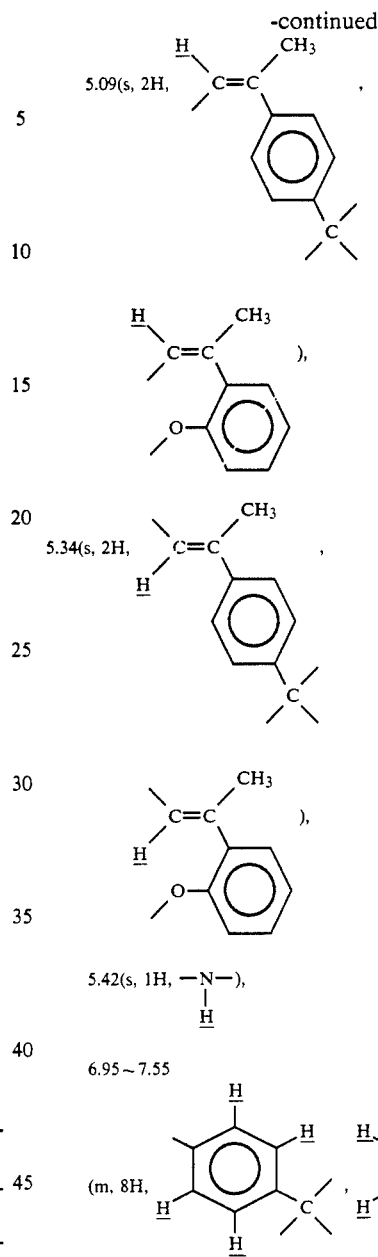

5.09(s, 2H, ...),

), 5.34(s, 2H, ...),

), 5.42(s, 1H, —N—H), 6.95 ~ 7.55

(m, 8H, ...)

Example 7

17.8 parts of 2-(4parts of toluene, 20.1 parts of 3-isopropenyl-α,αisocyanate and 0.2 part of dibutyltin dilaurate were The mixture was then stirred for 1 hour, while a reaction solution temperature was maintained at 80° to carry out the reaction. After completion of the reaction, the reaction solution was concentrated. The resulting concentrate was then purified by chromatography, thereby obtaining 35.7 parts of N-(3-dimethylbenzyl)[2-(4-isopropenylphenoxy)ethyl]carbamate in the form of a colorless transparent liquid.

| Values of elemental analysis (as $C_{24}H_{29}NO_3$) | | | |
|---|---|---|---|
| | C | H | N |
| Found (%) | 75.73 | 7.68 | 3.71 |
| Calcd. (%) | 75.96 | 7.70 | 3.69 |

NMR (δ/CDCl₃)

δ = 1.68(s, 6H, 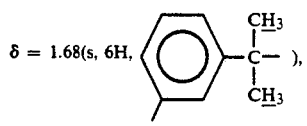), 2.13(s, 6H, 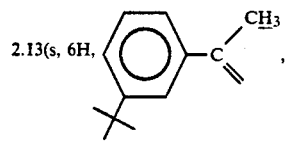),

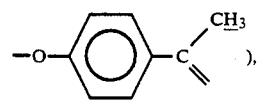), 4.13(s, 2H, —CH₂OCN—),
            ‖ |
            O H 4.35(s, 2H, —OCH₂—), 5.03(d, 2H, 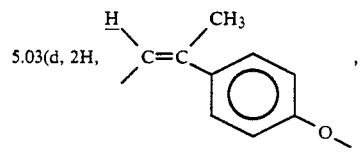,

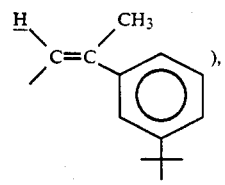), 5.06(s, 1H, —N—),
            |
            H 5.31(d, 2H, 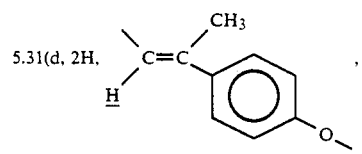,

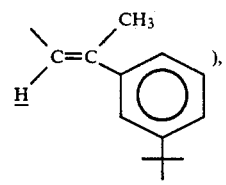), 6.86(d, 2H, 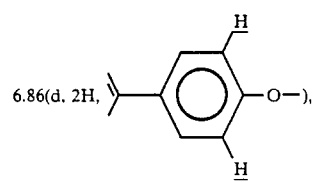), 7.31~7.48(m, 6H, 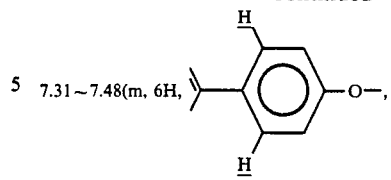,

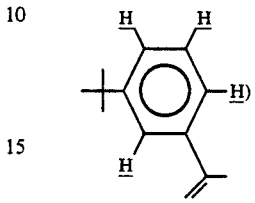)

Example 8

The same procedure as in Example 7 was repeated that 17.8 parts of 2-(4Example 7 was replaced with 17.8 parts of 2-isopropenylphenoxy)ethanol, thereby obtaining 36.3 parts of N-(3-dimethylbenzyl)[2-(3-isopropenylphenoxy)ethyl]carbamate in the form of a colorless transparent liquid.

| | Values of elemental analysis (as C₂₄H₂₉NO₃) | | |
|---|---|---|---|
| | C | H | N |
| Found (%) | 76.08 | 7.61 | 3.66 |
| Calcd. (%) | 75.96 | 7.70 | 3.69 |

NMR (δ/CDCl₃)

δ = 1.68(s, 6H, 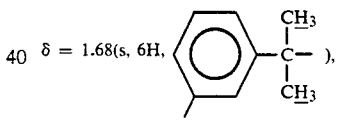), 2.13 (s, 6H, 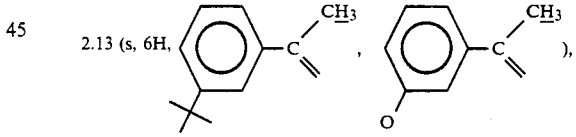), 4.15(s, 2H, —CH₂OCN—),
            ‖ |
            O H 4.36(s, 2H, —OCH₂—), 5.07(d, 2H, 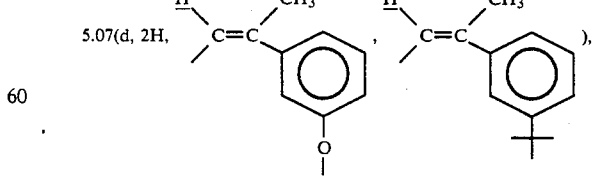), 5.21(s, 1H, —N—),
            |
            H

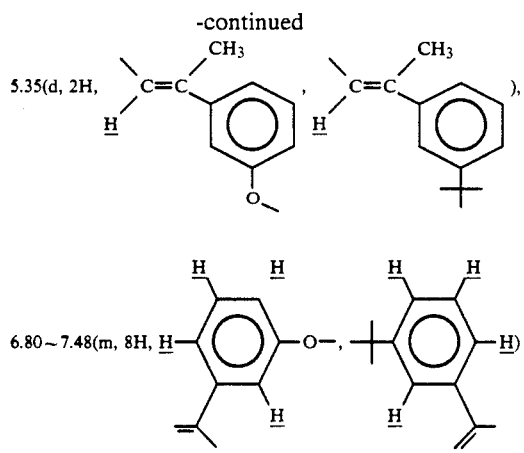

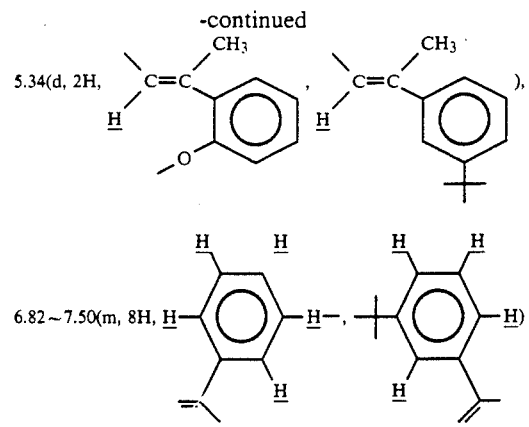

Example 9

The same procedure as in Example 7 was repeated that 17.8 parts of 2-(4Example 7 was replaced with 17.8 parts of 2-isopropenylphenoxy)ethanol, thereby obtaining 35.5 parts of N-(3-dimethylbenzyl)[2-(2-isopropenylphenoxy)ethyl]carbamate in the form of a colorless transparent liquid.

| Values of elemental analysis (as $C_{24}H_{29}NO_3$) | | | |
|---|---|---|---|
| | C | H | N |
| Found (%) | 75.83 | 7.65 | 3.63 |
| Calcd. (%) | 75.96 | 7.70 | 3.69 |

NMR($\delta$/CDCl$_3$)

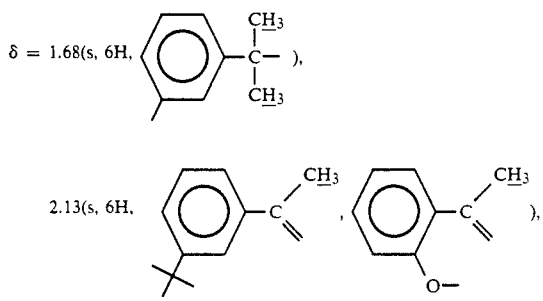

4.15(d, 2H, —CH$_2$OCN—),
            ‖ |
            O H 4.36(s, 2H, —OCH$_2$—),

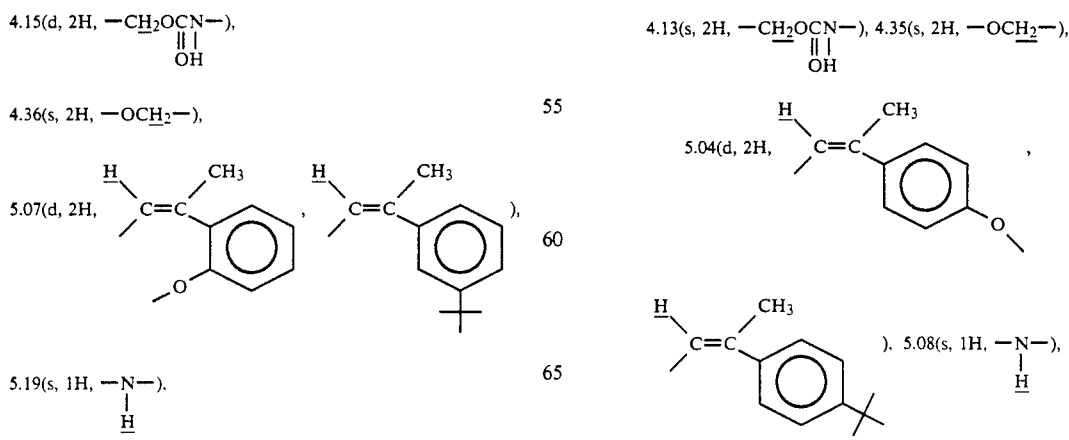

5.19(s, 1H, —N—).
         |
         H

Example 10

The same procedure as in Example 7 was repeated except that 20.1 parts of 3-isopropenyl-α,α-dimethylbenzyl isocyanate in Example 7 was replaced with 20.1 parts of 4-isopropenyl-α,α-dimethylbenzyl isocyanate, thereby obtaining 34.9 parts of N-(4-isopropenyl-α,α-dimethylbenzyl)-[2-(4-isopropenylphenoxy)ethyl] carbamate in the form of a colorless transparent liquid.

| Values of elemental analysis (as $C_{24}H_{29}NO_3$) | | | |
|---|---|---|---|
| | C | H | N |
| Found (%) | 76.13 | 7.78 | 3.76 |
| Calcd. (%) | 75.96 | 7.70 | 3.69 |

NMR ($\delta$/CDCl$_3$)

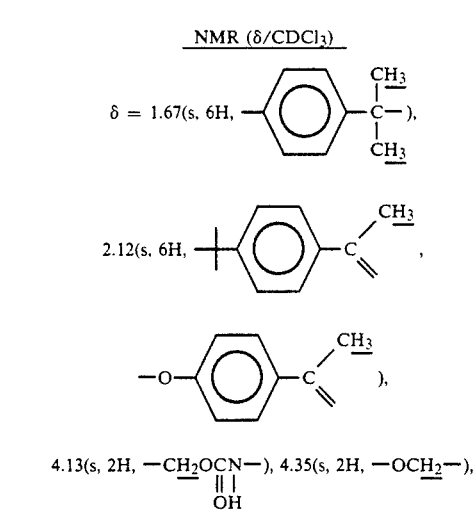

4.13(s, 2H, —CH$_2$OCN—), 4.35(s, 2H, —OCH$_2$—),
            ‖ |
            O H 5.08(s, 1H, —N—),
         |
         H

-continued
NMR (δ/CDCl₃)

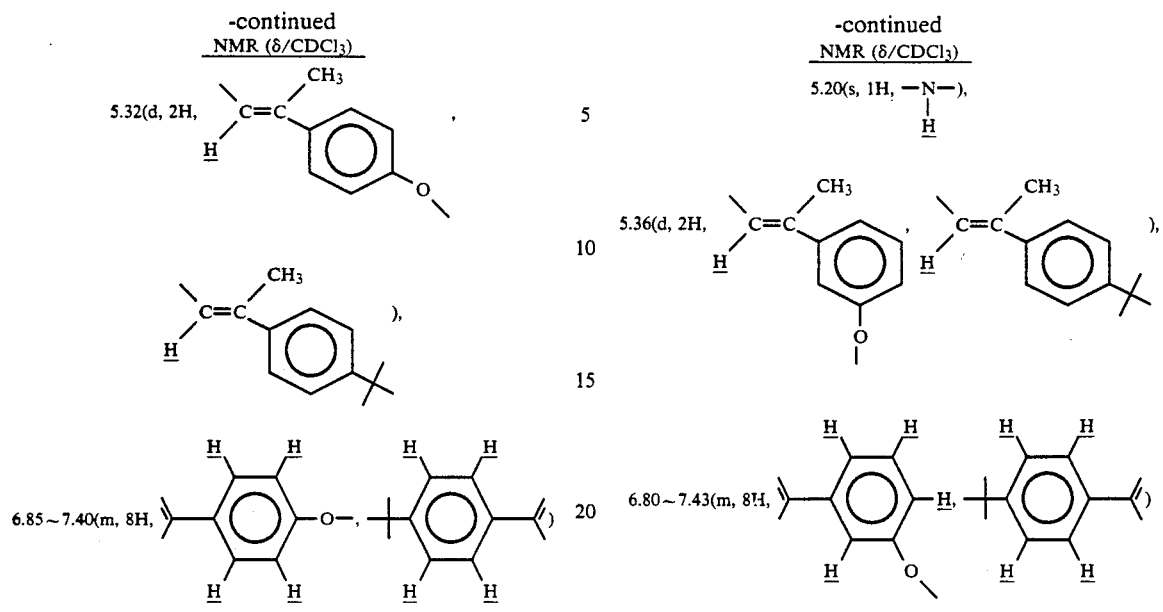

5.32(d, 2H, ...), 6.85~7.40(m, 8H, ...)

Example 11

The same procedure as in Example 8 was repeated except that 20.1 parts of 3-isopropenyl-α,α-dimethylbenzyl isocyanate in Example 8 was replaced with 20.1 parts of 4-isopropenyl-α,α-dimethylbenzyl isocyanate, thereby obtaining 35.1 parts of N-(4-isopropenyl-α,α-dimethylbenzyl) [2-(3-isopropenylphenoxy)ethyl] carbamate in the form of a colorless transparent liquid.

| Values of elemental analysis (as C₂₄H₂₉NO₃) | | | |
|---|---|---|---|
| | C | H | N |
| Found (%) | 75.99 | 7.64 | 3.48 |
| Calcd. (%) | 75.96 | 7.70 | 3.69 |

NMR (δ/CDCl₃)

δ = 1.67(s, 6H, ...), 2.12(s, 6H, ...), 4.13(s, 2H, —C<u>H</u>₂OCN—), 4.35(s, 2H, —OC<u>H</u>₂—),
     ‖ |
     O H 5.06(d, 2H, ...),

-continued
NMR (δ/CDCl₃)

5.20(s, 1H, —N—),
            |
            H

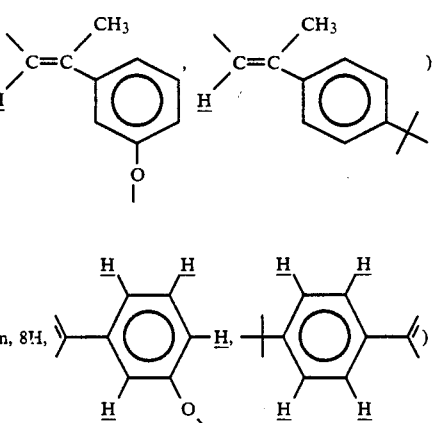

5.36(d, 2H, ...), 6.80~7.43(m, 8H, ...)

Example 12

The same procedure as in Example 9 was repeated except that 20.1 parts of 3-isopropenyl-α,α-dimethylbenzyl isocyanate in Example 9 was replaced with 20.1 parts of 4-isopropenyl-α,α-dimethylbenzyl isocyanate, thereby obtaining 35.8 parts of N-(4-isopropenyl-α,α-dimethylbenzyl) [2-(2-isopropenylphenoxy)ethyl] carbamate in the form of a colorless transparent liquid.

| Values of elemental analysis (as C₂₄H₂₉NO₃) | | | |
|---|---|---|---|
| | C | H | N |
| Found (%) | 75.84 | 7.71 | 3.65 |
| Calcd. (%) | 75.96 | 7.70 | 3.69 |

NMR (δ/CDCl₃)

δ = 1.67(s, 6H, ...), 2.12(s, 6H, ...), 4.12(s, 2H, —C<u>H</u>₂OCN—), 4.35(s, 2H, —OC<u>H</u>₂—),
     ‖ |
     O H

-continued
NMR (δ/CDCl₃)

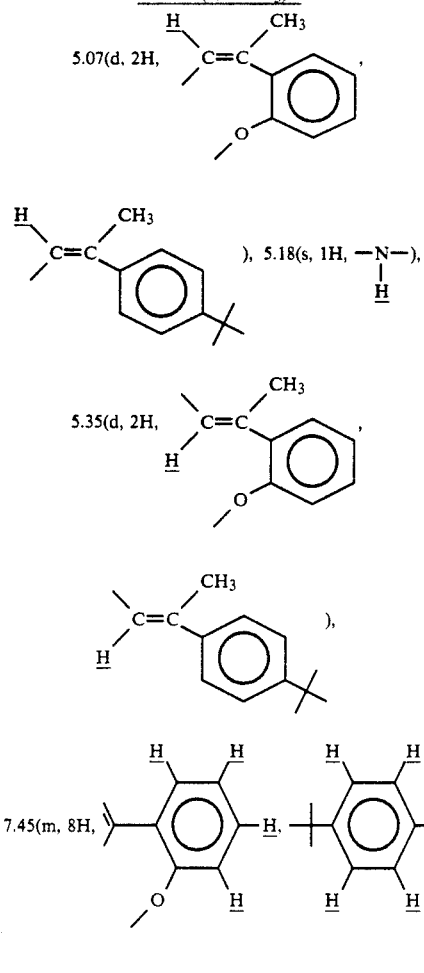

Example 13

The same procedure as in Example 7 was repeated except that 17.8 parts of 2-(4-isopropenylphenoxy)ethanol in Example 7 was replaced with 19.2 parts of 2-(4-isopropenylphenoxy)-1-methylethanol, thereby obtaining 37.0 parts of N-(3-isopropenyl-α,α-dimethylbenzyl) [2-(4-isopropenylphenoxy)-1-methylethyl] carbamate in the form of a colorless transparent liquid.

| Values of elemental analysis (as C₂₅H₃₁NO₃) | | | |
|---|---|---|---|
| | C | H | N |
| Found (%) | 76.15 | 7.99 | 3.47 |
| Calcd. (%) | 76.30 | 7.94 | 3.56 |

NMR (δ/CDCl₃)

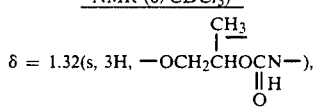

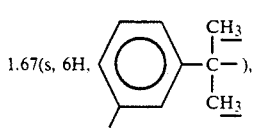

-continued
NMR (δ/CDCl₃)

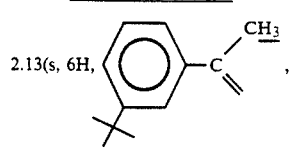

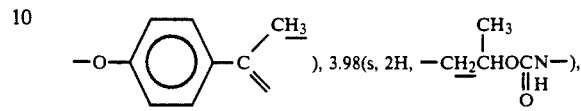

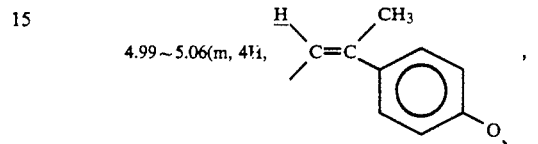

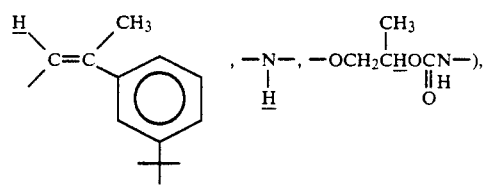

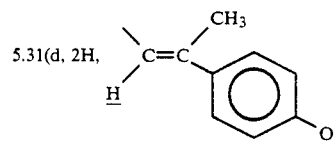

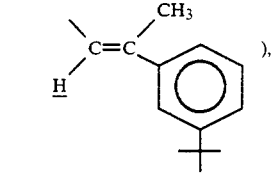

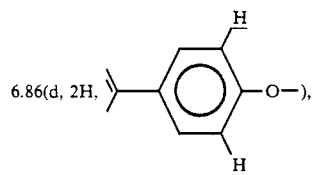

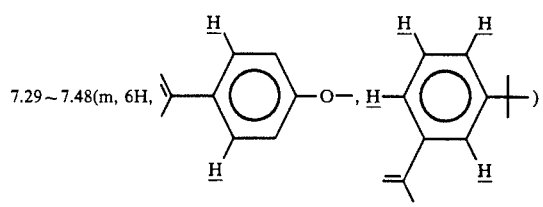

Example 14

The same procedure as in Example 8 was repeated except that 17.8 parts of 2-(3-isopropenylphenoxy)ethanol in Example 8 was replaced with 19.2 parts of 2-(3-isopropenylphenoxy)-1-methylethanol, thereby obtaining 36.3 parts of N-(3-isopropenyl-α,α-dimethylbenzyl) [2-(3-isopropenylphenoxy)-1-methylethyl] carbamate in the form of a colorless transparent liquid.

| Values of elemental analysis (as $C_{25}H_{31}NO_3$) | | | |
|---|---|---|---|
| | C | H | N |
| Found (%) | 76.41 | 8.08 | 3.37 |
| Calcd. (%) | 76.30 | 7.94 | 3.56 |

NMR ($\delta$/CDCl$_3$)

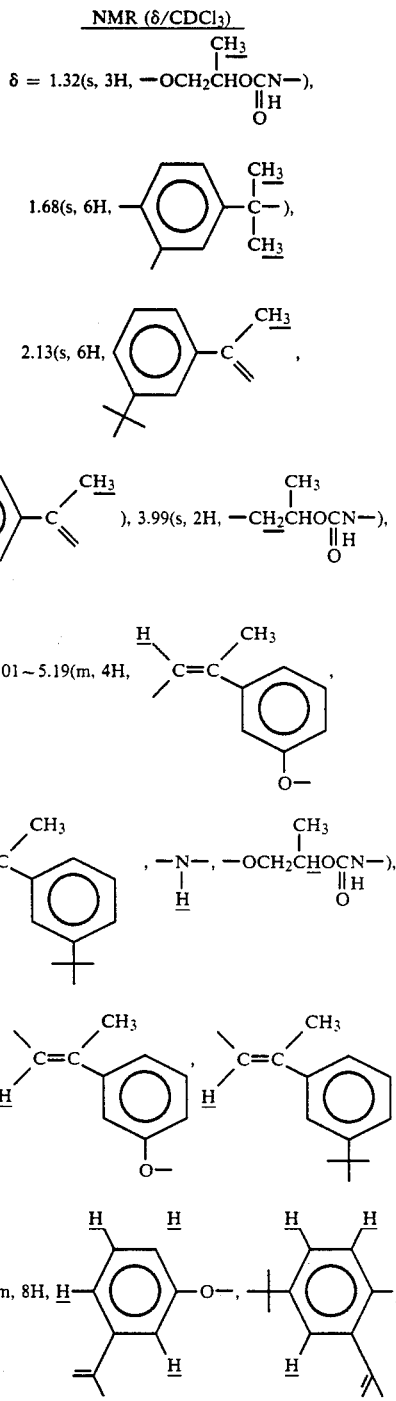

Example 15

The same procedure as in Example 9 was repeated except that 17.8 parts of 2-(2-isopropenylphenoxy)ethanol in Example 9 was replaced with 19.2 parts of 2-(2-isopropenylphenoxy)-1-methylethanol, thereby obtaining 35.2 parts of N-(3-isopropenyl-α,α-dimethylbenzyl) [2-(2-isopropenylphenoxy)-1-methylethyl] carbamate in the form of a colorless transparent liquid.

| Values of elemental analysis (as $C_{25}H_{31}NO_3$) | | | |
|---|---|---|---|
| | C | H | N |
| Found (%) | 76.18 | 7.69 | 3.58 |
| Calcd. (%) | 76.30 | 7.94 | 3.56 |

NMR ($\delta$/CDCl$_3$)

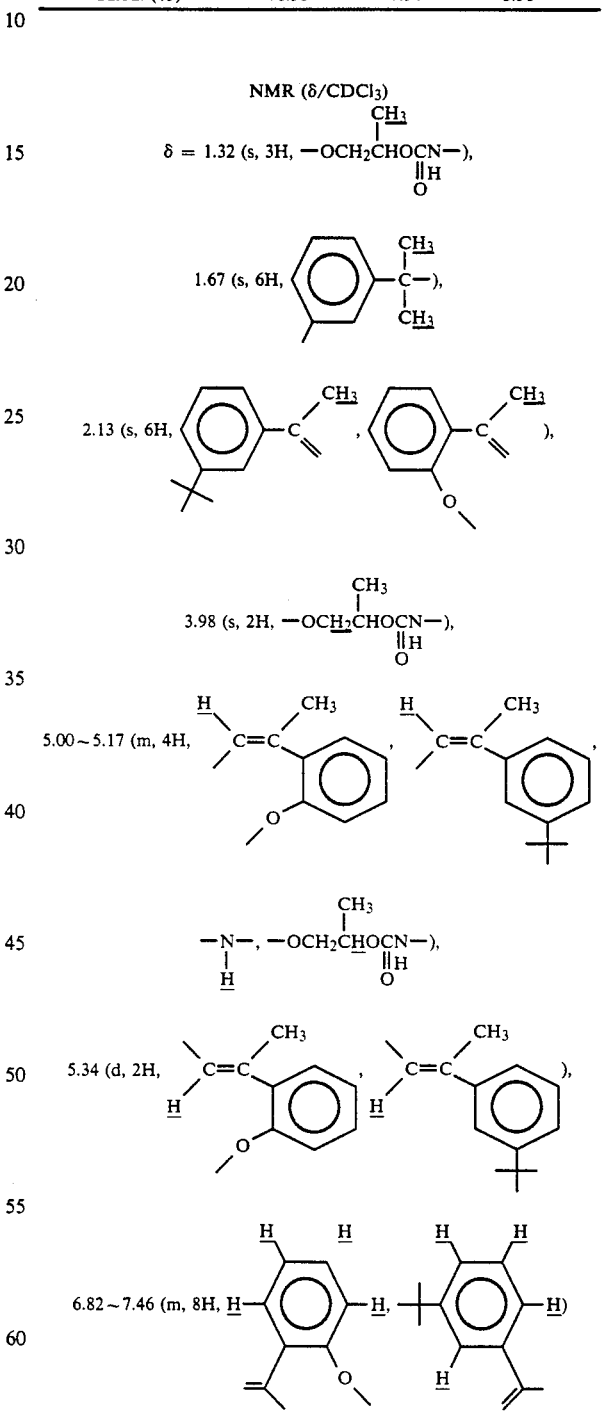

Example 16

The same procedure as in Example 13 was repeated except that 20.1 parts of 3-isopropenyl-α,α-dimethylbenzyl isocyanate in Example 13 was replaced with 20.1 parts of 4-isopropenyl-α,α-dimethylbenzyl isocyanate, thereby obtaining 35.9 parts of N-(4-isopropenyl-α,α-dimethylbenzyl)-[2-(4-isopropenylphenoxy)-1-methylethyl] carbamate in the form of a colorless transparent liquid.

| Values of elemental analysis (as $C_{25}H_{31}NO_3$) | | | |
|---|---|---|---|
| | C | H | N |
| Found (%) | 76.28 | 8.09 | 3.75 |
| Calcd. (%) | 76.30 | 7.94 | 3.56 |

NMR (δ/CDCl₃)

δ = 1.32 (s, 3H, —OCH₂CHOCN—),
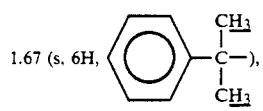

1.67 (s, 6H, 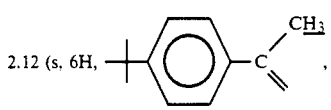

2.12 (s, 6H, 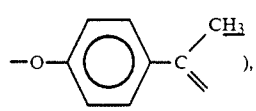

3.98 (s, 2H, —OCH₂CHOCN—), 5.00~5.08 (m, 4H, 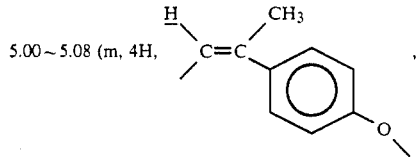

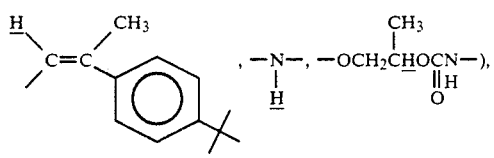

5.36 (d, 2H, 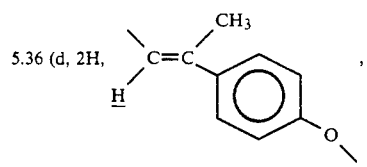

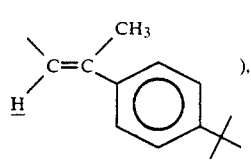 ),

-continued 6.81~7.44 (m, 8H, 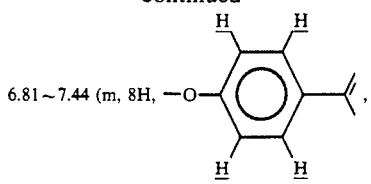,

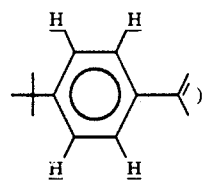 )

Example 17

The same procedure as in Example 14 was repeated except that 20.1 parts of 3-isopropenyl-α,α-dimethylbenzyl isocyanate in Example 14 was replaced with 20.1 parts of 4-isopropenyl-α,α-dimethylbenzyl isocyanate, thereby obtaining 37.1 parts of N-(4-isopropenyl-α,α-dimethylbenzyl)-[2-(3-isopropenylphenoxy)-1-methylethyl] carbamate in the form of a colorless transparent liquid.

| Values of elemental analysis (as $C_{25}H_{31}NO_3$) | | | |
|---|---|---|---|
| | C | H | N |
| Found (%) | 76.49 | 7.88 | 3.59 |
| Calcd. (%) | 76.30 | 7.94 | 3.56 |

NMR (δ/CDCl₃)

δ = 1.32 (s, 3H, —OCH₂CHOCN—), 1.67 (s, 6H, 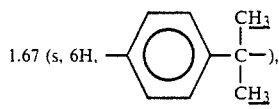

2.12 (s, 6H, 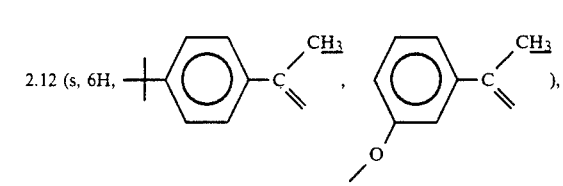 ), 3.98 (s, 2H, —OCH₂CHOCN—), 5.02~5.20 (m, 4H, 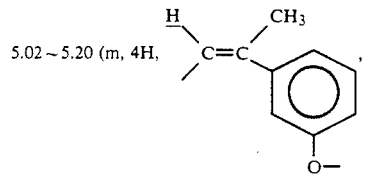, -continued

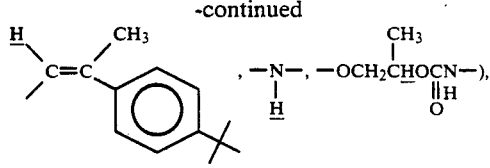, 5

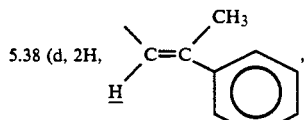, 10

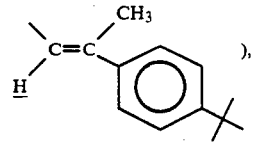), 20

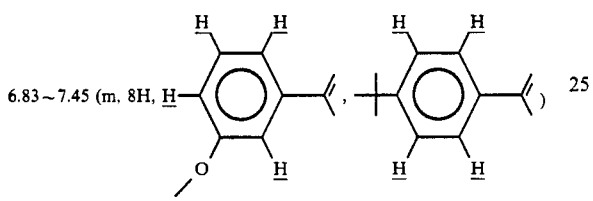

Example 18

The same procedure as in Example 15 was repeated except that 20.1 parts of 3-isopropenyl-α,α-dimethylbenzyl isocyanate in Example 15 was replaced with 20.1 parts of 4-isopropenyl-α,α-dimethylbenzyl isocyanate, thereby obtaining 36.4 parts of N-(4-isopropenyl-α,α-dimethylbenzyl)-[2-(2-isopropenylphenoxy)-1-methylethyl] carbamate in the form of a colorless transparent liquid.

| Values of elemental analysis (as $C_{25}H_{31}NO_3$) | | | |
|---|---|---|---|
| | C | H | N |
| Found (%) | 76.32 | 8.04 | 3.37 |
| Calcd. (%) | 76.30 | 7.94 | 3.56 |

NMR (δ/CDCl₃)

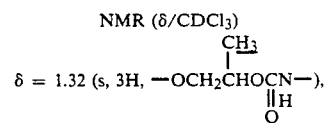

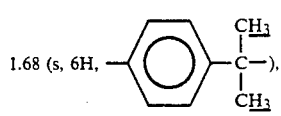

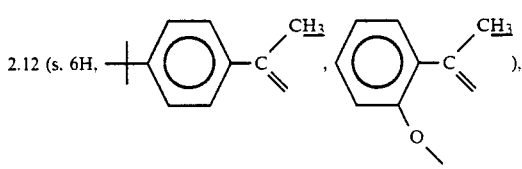

-continued

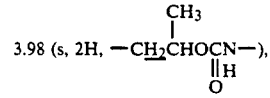

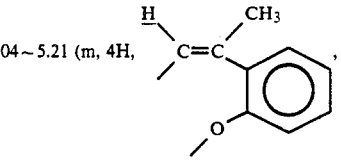

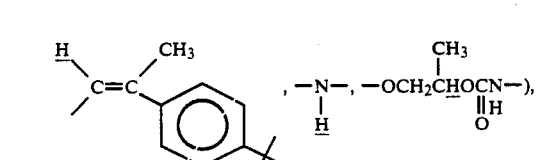

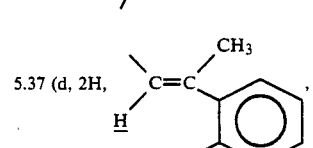

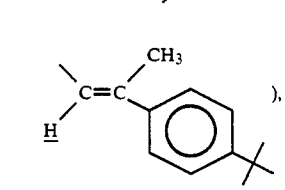

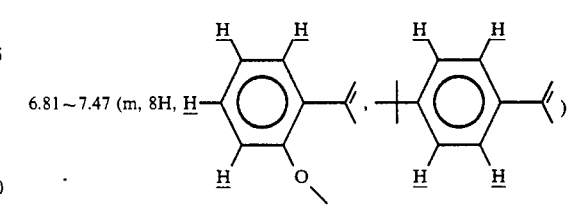

Example 19

71.2 parts of neopentyl glycol diacrylate and 0.4 part of benzoyl peroxide were added to 75.0 parts of [N-(3-isopropenyl-α,α-dimethylbenzyl)](4-isopropenylphenyl) carbamate obtained by the same procedure as in Example 1, followed by sufficient mixing and defoaming. The resulting uniform solution was then poured into a mold prepared by interposing a 5-mm-thick polyvinyl chloride spacer between peripheral portions of two 5-mm-thick glass plates and then firmly fastening them with a clamp. Polymerization was then effected in a hot-air oven for polymerization by elevating the temperature therein from 70° C. to 150° C. over 1.5 hours. After cooling, a transparent resin plate having a smooth surface was released from the mold.

Example 20

78.8 parts of pentaerythritol tetraacrylate and 0.5 part of benzoyl peroxide were added to 75.0 parts of [N-(3-isopropenyl-α,α-dimethylbenzyl)](3-isopropenylphenyl) carbamate obtained by the same procedure as in Example 2, followed by sufficient mixing and defoaming. The resulting uniform solution was then poured into a mold prepared by interposing a 5-mm-thick polyvinyl chloride spacer between peripheral portions of two 5-mm-thick glass plates, and then firmly fastening them with a clamp. Polymerization was then effected in a hot-air oven for polymerization by elevating the temperature therein from 70° C. to 150° C. over 1.5 hours. After cooling, a transparent resin plate having a smooth surface was released from the mold.

Example 21

58.7 parts of pentaerythritol tetraacrylate and 0.4 part of benzoyl peroxide were added to 63.3 parts of N-(3-isopropenyl-α,α-dimethylbenzyl)[2-(3-isopropenylphenoxy)ethyl] carbamate obtained by the same procedure as in Example 8, followed by sufficient mixing and defoaming. The resulting uniform solution was then poured into a mold prepared by interposing a 5-mm-thick polyvinyl chloride spacer between peripheral portions of two 5-mm-thick glass plates and then firmly fastening them with a clamp. Polymerization was then effected in a hot-air oven for polymerization by elevating the temperature therein from 70° C. to 150° C. over 1.5 hours. After cooling, a transparent resin plate having a smooth surface was released from the mold.

Example 22

43.4 parts of divinylbenzene and 0.3 part of benzoyl peroxide were added to 63.3 parts of N-(3-isopropenyl-α,α-dimethylbenzyl)[2-(3-isopropenylphenoxy)ethyl] carbamate obtained by the same procedure as in Example 8, followed by sufficient mixing and defoaming. The resulting uniform solution was then poured into a mold prepared by interposing a 5-mm-thick polyvinyl chloride spacer between peripheral portions of two 5-mm-thick glass plates and then firmly fastening them with a clamp. Polymerization was then effected in a hot-air oven for polymerization by elevating the temperature therein from 70° C. to 150° C. over 1.5 hours. After cooling, a transparent resin plate having a smooth surface was released from the mold.

Example 23

49.5 parts of trimethylolpropane trimethacrylate and 0.3 part of benzoyl peroxide were added to 65.6 parts of N-(3-isopropenyl-α,α-dimethylbenzyl)[2-(3-isopropenylphenoxy)-1-methylethyl] carbamate obtained by the same procedure as in Example 14, followed by sufficient mixing and defoaming. The resulting solution was then poured into a mold prepared by interposing a 5-mm-thick polyvinyl chloride spacer between peripheral portions of two 5-mm-thick glass plates and then firmly fastening them together with a clamp. Polymerization was then effected in a hot-air oven for polymerization by elevating the temperature therein from 70° C. to 150° C. over 1.5 hours. After cooling, a transparent resin plate having a smooth surface was released from the mold.

Example 24

3.3 parts of N-(3-isopropenyl-α,α-dimethylbenzyl)-2-methacryloyloxy carbamate, 77.5 parts of pentaerythritol tetraacrylate and 0.5 part of benzoyl peroxide were added to 63.3 parts of N-(3-isopropenyl-α,α-dimethylbenzyl)[2-(4-isopropenylphenoxy)ethyl] carbamate obtained by the same procedure as in Example 7, followed by sufficient mixing and defoaming. The resulting solution was then poured into a mold prepared by interposing a 5-mm-thick polyvinyl chloride spacer between peripheral portions of two 5-mm-thick glass plates and then firmly fastening them with a clamp. Polymerization was then effected in a hot-air oven for polymerization by elevating the temperature therein from 70° C. to 150° C. over 1.5 hours. After cooling, a transparent resin plate having a smooth surface was released from the mold. p For the transparent resin plates obtained in Examples 19 to 24, various physical properties were measured. The results are set forth in Table 1.

In measuring these physical properties, the following procedures were employed:

(1) Appearance: The appearance of each polymer plate was evaluated by observing the same by the naked eye. The polymer plates which were free from cracks and a rough surface were denoted by "O", and the plates having such disadvantages were denoted by "X".

(2) Surface Hardness: This was measured by the use of a pencil scratching test machine for coating films under JIS-K-5401.

(3) Heat Resistance: The resin plates were allowed to stand at 120° C. for 4 hours in a hot-air drier. Afterward, the resin plates were observed by the naked eye. The plates which were free from coloring and strain on the surfaces thereof were denoted by "O" and the plates having such drawbacks were denoted by "X".

(4) Chemical Resistance: The polymer plates were immersed in isopropanol and toluene at room temperature for 24 hours. Afterward, they were scratched with an HB pencil. The plates which were free from any traces were denoted by "O", and the plates having some traces were denoted by "X".

(5) Workability: The plates which could be abraded by a lens polisher for spectacle lens processing were denoted by "O", and the plates which could not be done were denoted by "X".

TABLE 1

| Test Item | Example 19 | Example 20 | Example 21 | Example 22 | Example 23 | Example 24 |
|---|---|---|---|---|---|---|
| Appearance | O | O | O | O | O | O |
| Surface Hardness | 4H | 9H or more | 9H or more | 5H | 4H | 9H or more |
| Heat Resistance | O | O | O | O | O | O |
| Chemical Resistance | O | O | O | O | O | O |
| Workability | O | O | O | O | O | O |

Example 25

0.1 part of benzoyl peroxide was added to 30.0 parts of a monomer mixture prepared by the same procedure as in Example 19, followed by mixing and defoaming and the mixture was then filtered through a filter having a pore diameter of 5 μm under pressure. The filtrate was then poured into a +2 diopter lens mold for diethylene glycol diallyl carbonate. Afterward, polymerization was effected by elevating the temperature of the mixture from 70° C. to 140° C. over 3 hours. After cooling, a transparent convex lens having a smooth surface was released from the mold. The pencil hardness on the surface of the convex lens was 4H, and the refractive index by the Abbe's refractometer was 1.53.

Example 26

0.2 part of benzoyl peroxide was added to 30.0 parts of a monomer mixture prepared by the same procedure as in Example 20, followed by mixing and defoaming and the mixture was then applied onto a steel plate by the use of a coating bar to form a coating thickness of 50 μm. Afterward, the mixture was cured at a temperature of 150° C. for 30 minutes, whereby a transparent coating film having a smooth surface was obtained on the steel plate. The pencil hardness of this coating film was 8H, and the results of a checker test (JIS K 5400) were good. In addition, heat resistance was also good (the specimens were allowed to stand at 120° C. for 10 hours in a hot-air drier, and those which were free from any problems were evaluated to be good).

Comparative Example 1

3.0 parts of benzoyl peroxide was added to 100 parts of diethylene glycol diallyl carbonate, followed by mixing and defoaming. This solution was then poured into a mold prepared by interposing a 5-mm-thick polyvinyl chloride spacer between peripheral portions of two 5-mm-thick glass plates and then firmly fastening them together with a clamp. Polymerization was attempted in a hot-air oven for polymerization by elevating the temperature therein from 70° C. to 120° C. over 3 hours. However, when the temperature reached about 70° C. in the course of the polymerization, the polymerization advanced vigorously, so that the polymer was peeled from the glass mold and was colored yellow.

Only when the polymerization was carried out by elevating the temperature from 50° C. to 120° C. over 10 hours, could a resin plate be obtained without peeling from the mold, but the pencil hardness of the obtained resin was 3H.

Comparative Example 2

18.8 parts of m-xylylene diisocyanate was added to 20.0 parts of methyl methacrylate, and 0.5 part of dibutyltin laurate was further added thereto. 26.0 parts of hydroxyethyl methacrylate was slowly added thereto, while heating was carried out so that an internal temperature might be 60° C., thereby obtaining a viscous methyl methacrylate mixture of an urethane compound in which the infrared spectrum absorption based on an isocyanate group was scarcely seen. 0.3 part of benzoyl peroxide was further added thereto, followed by mixing and defoaming. The solution was then poured into a mold prepared by interposing a 5-mm-thick polyvinyl chloride spacer between peripheral portions of two 5-mm-thick glass plates and then firmly fastening them together with a clamp.

Polymerization was attempted in a hot-air oven for polymerization by elevating the temperature therein from 45° C. to 120° C. over 3 hours. However, when the temperature reached about 65° C. in the course of the polymerization, the polymerization advanced vigorously, so that the polymer was peeled from the glass mold.

Comparative Example 3

0.5 part of benzoyl peroxide was added to 50 parts of trimethylolpropane triacrylate, followed by mixing and defoaming. This solution was then poured into a mold prepared by interposing a 5-mm-thick polyvinyl chloride spacer between peripheral portions of two 5-mm-thick glass plates and then firmly fastening them together with a clamp.

Polymerization was attempted in a hot-air oven for polymerization by elevating the temperature therein from 60° C. to 140° over 3 hours. However, at an early stage in the course of the polymerization, the polymerization advanced vigorously, so that the polymer was peeled from the glass mold.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A polymerizable monomer for a high surface hardness transparent resin represented by the formula

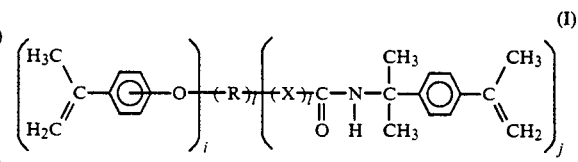

wherein R is an aliphatic residue having or not having an oxygen atom, an alicyclic ring, a heterocyclic ring or an aromatic ring, or an alicyclic residue, l is 0 or 1, each of i and j is an integer of 1 or more, and when l=0, i=j=1, when l=1, (i+j) is 4 or less, when j=1, X is oxygen or sulfur, when j≧2, all X's are oxygen or sulfur, or one X is oxygen and the other X's are sulfur, or one X is sulfur and the other X's are oxygen.

2. A polymerizable monomer for a high surface hardness transparent resin of claim 1 wherein X is an oxygen atom.

3. A polymerizable monomer for a high surface hardness transparent resin represented by the formula (VIII)

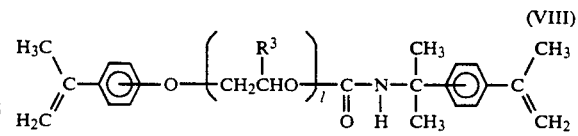

wherein l is 0 or 1, $R^3$ is selected from the group consisting of —H and —$CH_3$, and the substituents on the aromatic ring of the isopropenyl-α,α-dimethylbenzyl group are present at the m-position or p-position, and the substituents on the aromatic ring of the isopropenylphenoxy group are present at the o-position, m-position or p-position.

* * * * *